US00PP17810P2

(12) United States Plant Patent
Westhoff

(10) Patent No.: US PP17,810 P2
(45) Date of Patent: Jun. 12, 2007

(54) *OSTEOSPERMUM* PLANT NAMED 'WESOSORA'

(50) Latin Name: *Osteospermum ecklonis*
Varietal Denomination: Wesosora

(75) Inventor: Heinrich Westhoff, Südlohn (DE)

(73) Assignee: J. + H. Westhoff Interpel, Südlohn (DE)

( * ) Notice: Subject to any disclaimer, the term of this patent is extended or adjusted under 35 U.S.C. 154(b) by 0 days.

(21) Appl. No.: 11/323,161

(22) Filed: Dec. 30, 2005

(51) Int. Cl.
*A01H 5/00* (2006.01)

(52) U.S. Cl. ..... Plt./360
(58) Field of Classification Search ..... Plt./360
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Osteospermum* plant named 'Wesosora', characterized by its upright, compact and mounded plant habit; freely branching habit; freely and continuous flowering habit; and inflorescences with bright orange-colored ray florets.

1 Drawing Sheet

Botanical designation: *Osteospermum ecklonis.*
Botanical denomination: 'Wesosora'.

BACKGROUND OF THE INVENTION

The present Invention relates to a new and distinct cultivar of *Osteospermum* plant, botanically known as *Osteospermum ecklonis,* and hereinafter referred to by the name 'Wesosora'.

The new *Osteospermum* is a product of a planned breeding program conducted by the Inventor in Südlohn, Germany. The objective of the breeding program was to create new compact and freely flowering *Osteospermum* cultivars with attractive inflorescences.

The new *Osteospermum* originated from a cross-pollination in 2002 of a proprietary *Osteospermum ecklonis* selection identified as code number 02P05, not patented, as the female, or seed, parent with a proprietary *Osteospermum ecklonis* selection identified as code number 02P25, not patented, as the male, or pollen, parent. The new *Osteospermum* was discovered and selected by the Inventor as a single flowering plant within the progeny of the stated cross-pollination grown in a controlled environment in Südlohn, Germany.

Asexual reproduction of the new *Osteospermum* by terminal vegetative cuttings was first conducted in Südlohn, Germany in 2003. Asexual reproduction by cuttings has shown that the unique features of this new *Osteospermum* are stable and reproduced true to type in successive generations.

SUMMARY OF THE INVENTION

The cultivar Wesosora has not been observed under all possible environmental conditions. The phenotype may vary somewhat with variations in environment such as temperature and light intensity without, however, any variance in genotype.

The following traits have been repeatedly observed and are determined to be the unique characteristics of 'Wesosora'. These characteristics in combination distinguish 'Wesosora' as a new and distinct *Osteospermum:*

1. Upright, compact and mounded plant habit.
2. Freely branching habit.
3. Freely and continuous flowering habit.
4. Inflorescences with bright orange-colored ray florets.

Plants of the new *Osteospermum* differ from plants of the female parent selection in the following characteristics:

1. Plants of the new *Osteospermum* are more compact than plants of the female parent selection.
2. Plants of the new *Osteospermum* have broader leaves than plants of the female parent selection.
3. Plants of the new *Osteospermum* are more freely flowering than plants of the female parent selection.

Plants of the new *Osteospermum* differ from plants of the male parent selection in the following characteristics:

1. Plants of the new *Osteospermum* are more freely branching than plants of the male parent selection.
2. Plants of the new *Osteospermum* and the male parent selection differ in ray floret coloration as plants of the male parent have white to light yellow-colored ray florets.

Plants of the new *Osteospermum* can be compared to plants of the cultivar Sumost 02, disclosed in U.S. Plant Pat. No. 15,975. In side-by-side comparisons, plants of the new *Osteospermum* differed from plants of the cultivar Sumost 02 in the following characteristics:

1. Plants of the new *Osteospermum* were more compact than plants of the cultivar Sumost 02.
2. Plants of the new *Osteospermum* were more freely branching than plants of the cultivar Sumost 02.
3. Plants of the new *Osteospermum* had broader and lighter green-colored foliage than plants of the cultivar Sumost 02.
4. Plants of the new *Osteospermum* had smaller inflorescences with fewer ray florets than plants of the cultivar Sumost 02.

Plants of the new *Osteospermum* can also be compared to plants of the cultivar Sumost 01, disclosed in U.S. Plant Pat. No. 15,296. In side-by-side comparisons, plants of the new *Osteospermum* differed from plants of the cultivar Sumost 01 in the following characteristics:

1. Plants of the new *Osteospermum* were more compact than plants of the cultivar Sumost 01.
2. Plants of the new *Osteospermum* were more freely branching than plants of the cultivar Sumost 01.
3. Plants of the new *Osteospermum* had lighter green-colored foliage than plants of the cultivar Sumost 01.
4. Plants of the new *Osteospermum* had smaller inflorescences with fewer ray and disc florets than plants of the cultivar Sumost 01.
5. Plants of the new *Osteospermum* and the cultivar Sumost 01 differed in ray floret coloration as plants of the cultivar Sumost 01 had yellow-colored ray florets.

BRIEF DESCRIPTION OF THE PHOTOGRAPHS

The accompanying colored photographs illustrate the overall appearance of the new *Osteospermum* showing the colors as true as it is reasonably possible to obtain in colored reproductions of this type. Colors in the photographs may differ from the color values cited in the detailed botanical description which accurately describe the colors of the new *Osteospermum.*

The photograph at the top of the sheet comprises a side perspective view of a typical flowering plant of 'Wesosora' grown in a container.

The photograph at the bottom of the sheet is a close-up view of a typical inflorescence of 'Wesosora'.

DETAILED BOTANICAL DESCRIPTION

The new *Osteospermum* has not been observed under all possible environmental conditions. The phenotype may vary somewhat with variations in environment such as temperature and light intensity, without, however, any variance in genotype.

The aforementioned photograph, following observations and measurements describe plants grown in Südlohn, Germany in a glass-covered greenhouse during the spring and summer and under commercial production practices. Plants were about 20 weeks from planting rooted young plants when the photographs and description were taken. During the production of the plants, day temperatures ranged from 20° C. to 25° C. and night temperatures ranged from 16° C. to 18° C. Plants were pinched one time about three to four weeks after planting. In the following description, color references are made to The Royal Horticultural Society Colour Chart, 2001 Edition, except where general terms of ordinary dictionary significance are used.

Botanical classification: *Osteospermum ecklonis* cultivar Wesosora.

Parentage:

*Female, or seed, parent.*—Proprietary selection of *Osteospermum ecklonis* identified as code number 02P05, not patented.

*Male, or pollen, parent.*—Proprietary selection of *Osteospermum ecklonis* identified as code number 02P25, not patented.

Propagation:

*Type.*—Terminal vegetative cuttings.

*Time to initiate rooting, summer.*—About 14 to 16 days at 18° C. to 20° C.

*Time to initiate rooting, winter.*—About 16 to 18 days at 18° C. to 20° C.

*Time to produce a rooted young plant, summer.*—About 18 to 21 days at 18° C. to 20° C.

*Time to produce a rooted young plant, winter.*—About 21 to 24 days at 18° C. to 20° C.

*Root description.*—Fine, fibrous.

*Rooting habit.*—Freely branching.

Plant description:

*Plant form and growth habit.*—Perennial herbaceous container and garden plant. Upright, compact and mounded plant habit; inverted triangle. Freely branching habit, about seven to twelve lateral branches per plant.

*Plant height.*—About 12.6 cm.

*Plant width or area of spread.*—About 15.8 cm.

*Lateral branches.*—Length: About 9.2 cm. Diameter: About 3.5 mm. Internode length: About 1 cm. Aspect: Mostly upright. Strength: Strong. Texture: Pubescent. Color: 146D.

*Foliage description.*—Arrangement: Alternate, simple; sessile. Length: About 6.8 cm. Width: About 2 cm. Shape: Oblanceolate. Apex: Rounded to slightly cuspidate. Base: Attenuate. Margin: Entire with several indentations. Venation pattern: Pinnate. Texture, upper and lower surfaces: Smooth, glabrous. Color: Developing foliage, upper surface: 146A and 146C. Developing foliage, lower surface: 146B. Fully expanded foliage, upper surface: 137A; venation, 147C. Fully expanded foliage, lower surface: 137C; venation, 147C to 147D.

Inflorescence description:

*Appearance.*—Solitary terminal and axillary inflorescences held above and beyond the foliage on strong peduncles. Composite inflorescence form, radially symmetrical, with ligulate-shaped ray florets and disc florets massed at the center; ray and disc florets develop acropetally on a capitulum. Inflorescences not persistent. Inflorescences face mostly upright.

*Flowering response.*—Plants flower continuous and freely from April through the fall in Germany.

*Postproduction longevity.*—Inflorescences maintain good color and substance for about one week on the plant.

*Fragrance.*—None detected.

*Inflorescence bud.*—Length: About 1.2 cm. Diameter: About 5 mm to 7 mm. Shape: Ovoid. Color: Towards the base, 145A; towards the apex, 138A.

*Inflorescence size.*—Diameter: About 4.5 cm. Depth (height): About 1.2 cm. Disc diameter: About 7 mm. Receptacle height: About 4.5 mm. Receptacle diameter: About 9 mm.

*Ray florets.*—Length: About 2 cm to 2.3 cm. Width: About 6 mm. Shape: Ligulate. Apex: Slightly emarginate. Base: Acute, fused into a tube. Margin: Entire. Texture, upper and lower surfaces: Smooth, glabrous; satiny. Number of ray florets per inflorescence: About 17 in a single whorl. Aspect: Initially upright, with development, about 45° to 50° from vertical. Color: When opening, upper surface: 25A; at the base, N89A to N89B. When opening, lower surface: 172B to 172C. Fully opened, upper surface: 28C to 29A; at the base, N89C. Fully opened, lower surface: N172B to N172C.

*Disc florets.*—Shape: Tubular, elongated. Apex: Five-pointed. Length: About 5 mm. Width: At apex: About 1 mm. At base: Less than 1 mm. Number of disc florets per inflorescence: About 70. Color: Immature: N92A to N92C. Mature: Apex: N92C. Mid-section: 76B. Base: 76C.

*Phyllaries.*—Length: About 1.2 cm. Diameter: About 2 mm. Shape: Apiculate. Apex: Acute. Base: Fused. Margin: Entire. Texture, upper and lower surfaces: Pubescent. Number per inflorescence: About 17. Color, upper and lower surfaces: 137C; towards the margin, 138D.

*Peduncles.*—Length, terminal peduncle: About 4.2 cm to 4.7 cm. Length, second peduncle: About 3.6 cm. Diameter: About 1.5 to 2 mm. Angle: Terminal peduncles, mostly upright; axillary peduncles about 45° from stem axis. Strength: Strong; flexible. Texture: Pubescent. Color: 146B.

*Reproductive organs.*—Androecium: Present on disc florets only. Stamen number: Five per floret; fused around style. Anther shape: Oblong. Anther length: Less than 1 mm. Anther color: 79A. Pollen amount: Moderate to scarce. Pollen color: 25A. Gynoecium: Present on both ray and disc florets. Pistil number: One per floret. Pistil length: About 8 mm. Stigma shape: Two-parted. Stigma color: 79B. Style length: About 4.5 mm. Style color: 36D to 84B to 84C. Ovary color: 145C to 145D.

*Seeds/fruits.*—Seed and fruit production has not been observed on plants of the new *Osteospermum.*

Disease/pest resistance: Resistance to pathogens and pests common to *Osteospermums* has not been observed on plants grown under commercial greenhouse conditions.

Temperature tolerance: Plants of the new *Osteospermum* have been observed to tolerate temperatures from about 5° C. to about 30° C.

It is claimed:

1. A new and distinct cultivar of *Osteospermum* plant named 'Wesosora', as illustrated and described.

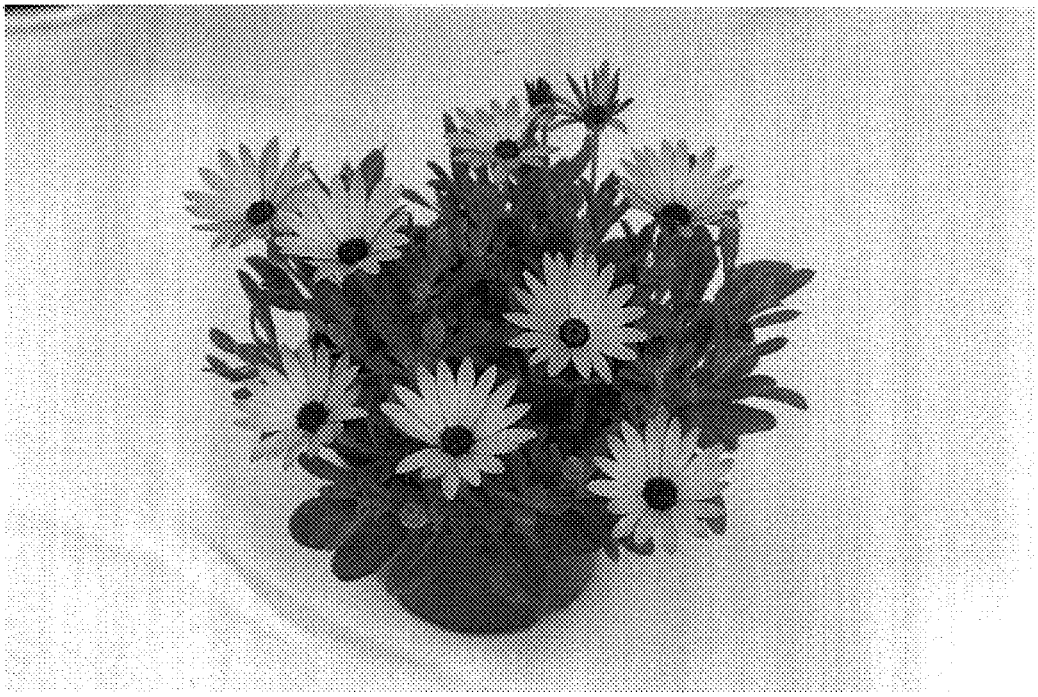
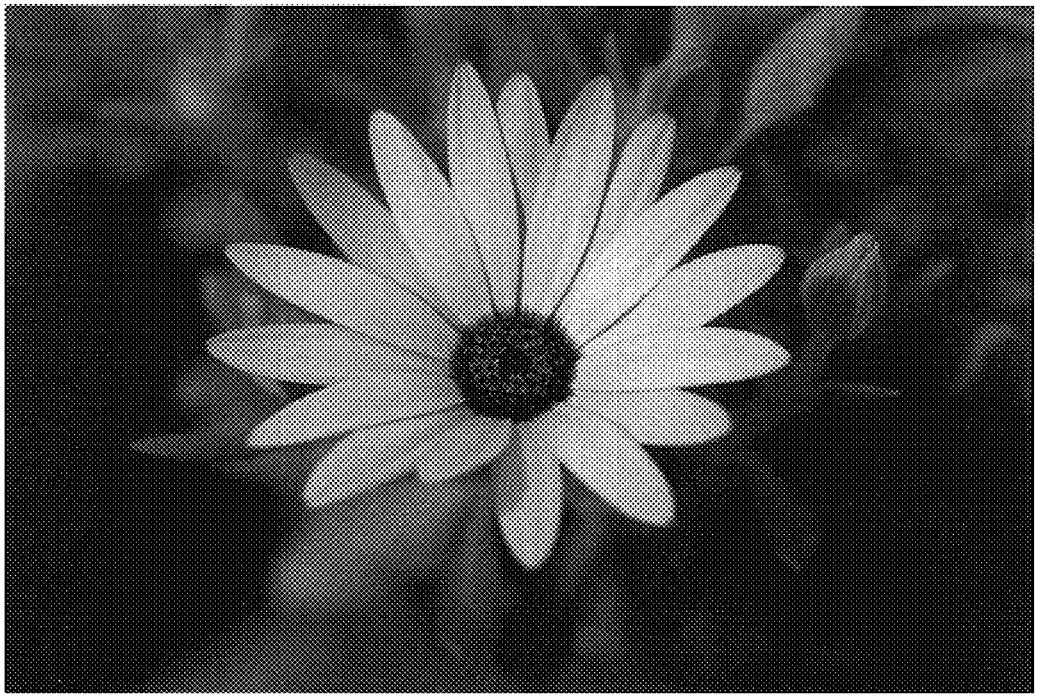

* * * * *